(12) United States Patent
Donaghue et al.

(10) Patent No.: US 6,885,007 B2
(45) Date of Patent: Apr. 26, 2005

(54) RADIATION DETECTION APPARATUS

(75) Inventors: David M. Donaghue, Cleveland, OH (US); Robert L. White, Medina, OH (US); Leonard W. Zimmermann, Lakewood, OH (US)

(73) Assignee: Cardinal Health 419, L.L.C., Dublin, OH (US)

( * ) Notice: Subject to any disclaimer, the term of this patent is extended or adjusted under 35 U.S.C. 154(b) by 40 days.

(21) Appl. No.: 10/210,764

(22) Filed: Aug. 1, 2002

(65) Prior Publication Data

US 2005/0056791 A1 Mar. 17, 2005

(51) Int. Cl.[7] .............................. G01J 1/42; G01T 1/00
(52) U.S. Cl. .................. 250/394; 250/200; 250/370.01
(58) Field of Search ................. 250/394, 200, 250/370.01, 370.03, 370.07, 370.1, 374

(56) References Cited

U.S. PATENT DOCUMENTS

| | | |
|---|---|---|
| 2,953,702 A | 9/1960 | Zieler |
| 4,970,398 A | 11/1990 | Scheid |
| 4,988,866 A * | 1/1991 | Westerlund .............. 250/252.1 |
| 5,308,988 A | 5/1994 | Siedband |
| 5,508,526 A | 4/1996 | Labbe |
| 5,621,214 A * | 4/1997 | Sofield ...................... 250/375 |
| 6,125,335 A * | 9/2000 | Simon et al. ................ 702/85 |

OTHER PUBLICATIONS

Victoreen, Inc.; Instruction Manual, "THEBES® Therapy Beam Evaluation System Model 7000"; revised version 12/96.

* cited by examiner

*Primary Examiner*—David Porta
*Assistant Examiner*—Christine Sung
(74) *Attorney, Agent, or Firm*—Woodard, Emhardt, Moriarty, McNett & Henry LLP

(57) ABSTRACT

A radiation detection system has a linear array of radiation detectors, which are preferably ionization chambers. The detectors are connected, preferably permanently, to a multi-channel signal processor through a flexible multi-conductor shielded cable. The multi-channel signal processor is connected to a controller, such as a personal computer, through a multi-conductor cable and a communication interface device. Multiple detector arrays and multi-channel electrometers may be connected to a single personal computer and used simultaneously.

35 Claims, 9 Drawing Sheets

RADIATION DETECTION APPARATUS

FIELD OF THE INVENTION

This invention concerns apparatus and methods for measuring the radiation emitted from a radiation source. In particular, the invention concerns an array of radiation detectors electronically linked to processing software and display apparatus for detecting the radiation emitted from medical radiation therapy sources.

BACKGROUND OF THE INVENTION

Radiation therapy treats tumorous tissue by delivering a prescribed lethal dose of high-energy radiation to the tumorous tissue. The dose and the placement of the dose must be accurately controlled to insure both that the tumor receives sufficient radiation to be destroyed and that damage to the surrounding and adjacent non-tumorous tissue is minimized. One type of such therapy, known as external-beam radiation therapy, uses a radiation source that is external to the patient. The source is typically either a radioisotope, such as cobalt-60, or a high-energy x-ray or electron source, such as a linear accelerator. The external source produces a collimated beam of radiation that is directed at the patient, toward the tumor site.

Accurate measurement of the radiation intensity profile of a radiotherapy beam is important in radiation therapy quality assurance, radiation therapy treatment planning or verification of treatment. The radiation intensity profile, as its name suggests, is a description of the characteristics of a radiotherapy beam, such as the sizes of the beam center, penumbras of the beam, and overall field, the degrees of flatness and symmetry of the beam, intensity (i.e. energy output) of the beam at given points, and/or other features. "Beam profile" generally indicates the size, shape or distribution of a beam, and "intensity" generally indicates the energy output of the beam. The ability to precisely characterize the radiation intensity profile also permits evaluation of any filters or attenuating blocks that may be used in conjunction with the radiation beam to shape or attenuate the radiation beam.

Several methods may be used to determine the intensity profile of a radiation beam. In one method, the beam is linearly scanned using a small radiation detector, typically an ionization chamber, within a tank of water, which simulates the patient radiation absorption characteristics. Another similar method uses a diode in place of the ion chamber and utilizes plastic material placed above the detector instead of water. The beam is scanned on an axis that is perpendicular to the beam axis, typically passing through the central axis of the beam. Some systems utilize a second detector, usually placed at iso-center, which is used to compensate for variations in beam intensity. In all beam-scanning systems, the detector generates a current that is proportional to the radiation intensity at each point in the scan. Typical water tank scanning systems include models MP3, MP3-S, MP3-XS, MP2, MP1, MP1-S, Type 4322, Type 41001, and Type 41014 manufactured by PTW Freiburg; Blue Phantom, RFA-200, RFA-300, and 2-D Phantom made by Wellhöfer; DynaScan Model 3112 manufactured by CMS; and Model 3000 and Model 2000 made by Advanced Radiation Measurements (ARM). A typical solid-state (diode) scanning system is the Nuclear Associates BeamScan.

This method has been widely accepted and offers several advantages over other methods. One of the primary advantages is the high spatial resolution (i.e. the ability to obtain precise readings) along the scanned axis, which is typically determined by the mechanical resolution of the scanning device or mechanism. Since only one or two detectors are used, another advantage is the low number of detectors and their associated readout electronics (electrometers). This reduces circuit complexity and limits the number of detectors that are required to be calibrated. Many of these systems offer beam scanning in three dimensions.

This method of beam scanning also has several limitations and drawbacks. One limitation concerns the measurement of dynamic radiation treatment modalities, such as wedge-shaped radiation dose distribution ("dynamic wedge") or intensity modulated radiation therapy (IMRT), in which the radiation intensity and/or beam profile changes over time. Quality assurance within such modalities requires measurements at many different points in the dynamic treatment to accurately characterize the beam dynamics over time. However, to accurately measure the beam profile using existing beam scanning methods as noted above, the beam profile must be static and its intensity must be constant during the scan, i.e. the beam cannot change over time. Variations in the beam profile or intensity during the time needed to scan the beam result in errors in the measured beam profiles. Accordingly, numerous separate measurements of radiation intensity profile, representing different points of static beam profile and constant intensity, must be made to fully characterize a dynamic treatment modality. A significant amount of time is generally required to make these measurements, which can become tedious. Further, operating a radiotherapy source for such extended time periods may also place undue stress on the source's and detector's components. The beam scanning system must be mechanically aligned properly and its positioning mechanisms must be accurate and reproducible. In addition, setting up and taking down a water tank and/or other beam scanning device can also be very time consuming and inconvenient.

A second method of measuring a beam's radiation intensity profile uses multiple detectors, such as ion chambers or diodes, in a linear array so as to simultaneously measure the beam intensity at numerous measurement points. Using this method, the detector array is placed perpendicular to the beam axis, typically passing through the central axis of the beam. Each detector generates a current that is proportional to the radiation intensity at its position in the array. Array detectors may be available with beam scanning devices that allow them to scan a beam to create a two dimensional beam profile image.

Making simultaneous measurements of radiation intensity profile with an array of detectors offers several advantages over the previously described beam scanning method. Since acquisition of data concerning the beam profile occurs simultaneously for all detectors in the array, several points on the beam profile are measured simultaneously to produce a "snapshot" of the beam profile at a specific moment in real time. This eliminates the need for multiple static beam profile measurements at many different points in a dynamic treatment. As a result, beam profile measurements may be made in real time for dynamic treatment modalities. This reduces stress on the radiotherapy source and is less tedious than the beam scanning method. It is often easier to set up and more convenient.

The limitations and disadvantages of this method result from the number of locations in the beam that must be sampled and the small size of the detectors required in order to generate an image of the beam profile with suitable spatial resolution. Moreover, simultaneous measurements by a detector array require readout electronics for each detector, typically an electrometer, to process the signal from each detector. It is known to place the detectors and readout electronics in close proximity on the same printed circuit board. In that scheme, however, radiation strikes both the detectors and the electronics, resulting in damage to the electronics that occurs with accumulated radiation dose. It is also known to place an interconnecting cable between the detectors and readout electronics, allowing the readout electronics to be located a distance from the radiation beam, significantly reducing the amount of radiation damage to the electronics. Collecting the small currents from a large number of detectors requires multiple coaxial low noise cables (or a multi-conductor cable with a conductor for each detector) to transfer the small detector signals to the readout electronics. However, the size and lack of flexibility of multi-conductor cables, or the number of individual cables, make such a system fairly cumbersome. The requirement for separate readout electronics for each detector also adds considerable cost to the system.

The spatial resolution of a detector array is also limited by the size of the detector. In an ion chamber array, for example, the detector size is limited by the signal-to-noise ratio of the detector. Since the current produced by an ion chamber detector is proportional to its volume (in a constant radiation flux), a smaller ion chamber produces a smaller signal and signal-to-noise performance is degraded. Accordingly, the ion chambers in an array cannot be so small that the noise overcomes the signal to the extent that the signal cannot produce a resolvable output.

The calibration requirements of a detector array also are a disadvantage. Each detector and its associated readout electronics must be individually calibrated in order to provide an accurate representation of a beam's radiation intensity profile. Additionally, all detectors must respond in the same way to variations in beam energy and intensity, to ensure accurate and precise readings for dynamic radiation treatment modalities.

Further, currently most detector arrays are not waterproof and cannot be used in a water tank to obtain beam profiles and intensities at various depths of water. Radiation beam quality assurance using a water tank to simulate treatment conditions is a well-known practice. Instead, to use non-waterproof detector arrays acrylic or plastic elements are stacked on top of the array to simulate water. Existing ionization chamber array systems include Thebes Model 7000 made by Victoreen; CA-24 made by Wellhöfer; and LA-48 made by PTW Freiburg.

When diodes are used as detectors for either of these beam-profiling methods (beam scanning or simultaneous measurements), their energy response changes and their sensitivity degrades with accumulated dose and must be corrected through frequent recalibration. The diodes must then be replaced when this degradation becomes significant. Existing solid-state detector array systems include Model 1170 Profiler and Model 1172 Solid-State Dosimetry (SSD) System made by Sun Nuclear; Hi-pSi Semiconductor Array made by Wellhöfer; and BMS 96 made by Schuster.

A third method of measuring the beam's radiation intensity profile uses film that is sensitive to x-ray or gamma radiation and a film scanner or densitometer to measure the optical density at many points on the exposed film. The exposed film density is proportional to the film's accumulated radiation exposure. To perform beam measurements by this method, the film is placed between layers of material whose radiological properties are similar to human tissue or water. The film is then placed at the desired position in the radiation beam, exposed, processed (if necessary) and scanned by a film scanner. Software is then used to convert the scanned results into a radiation intensity profile. Alternatively, a densitometer may be used to perform the film density measurements manually.

The primary advantage of this method is that it captures a high-resolution image of the beam intensity profile in two dimensions simultaneously. This allows a single film to be used to produce a two dimensional image of a static beam profile or an integrated two-dimensional image of a dynamic treatment profile.

This method has limitations when used for measurements of dynamic treatment modalities in which the radiation intensity and/or beam profile changes over time. This requires measurements at many different points in the dynamic treatment to accurately characterize the beam dynamics over time. In order to accurately measure the beam profile, the beam profile must be static and its intensity must constant during the film's exposure time. Variations in the beam profile or intensity during this time can result in errors in the measured beam profiles. A significant amount of time is generally required to expose, process and scan the films, which can become tedious. Operating a radiotherapy source for the extended time periods necessary to fully characterize a dynamic treatment may also place undo stress on its components. Further, accurate registration of the film with the beam is required to accurately translate the positional information from the film into actual positions within the beam. The film must also be aligned properly and its positioning must be accurate and reproducible. Like most detector arrays, however, film is not waterproof and typically cannot be used in a water tank to obtain beam profiles at various depths of water. Instead, film is stacked between acrylic or plastic water plates to simulate water. Typical film dosimetry systems include the DynaScan Model 1710 Laser Densitometer made by CMS; and the RIT 113 Radiation Therapy Film Dosimetry System made by RIT with a Vidar or Lumisys film scanner.

Accordingly, there is a need for an apparatus and methods for detection of radiation that is convenient, inexpensive, easy and quick to operate, and will limit the degradation resulting from contact with radiation.

SUMMARY OF THE INVENTION

The present invention, in one embodiment, is an apparatus comprising a plurality of radiation detectors, each of which is adapted to output a signal related to detected radiation, a signal processor communicatively connected to the detectors at a distance from them, wherein the signal processor receives signals from the detectors and outputs digital data related to the signals, and a display medium communicatively connected to the signal processor, whereby information of said data from said signal processor that is related to detected radiation is displayed. The detectors can be ion chambers or other known detectors, and they may be fashioned in an array, such as a linear array, with a waterproof and/or vented housing. The array may further include a printed circuit board for routing signals, and a second set of detectors for providing a pulse signal. The signal processor may include at least one electrometer, at least one analog-to-digital converter and a microcontroller. The detectors may be connected to the signal processor by a mass terminated multi-conductor shielded cable. The signal processor may be connected to a display, which preferably includes a controller (e.g. a personal computer), via a multi-conductor cable and interface. The signal processor provides data regarding detected radiation to the display, which displays the information in a format appropriate for a quality assurance technician.

In a preferred embodiment, the detectors are separated from the signal processor and display by a distance sufficient to be positioned away from the direct radiation beam, greatly reducing the potential for radiation damage to the signal processor and the display. In one specific embodiment, a cable is provided that allows the signal processor to be situated away from the radiation beam, and such a cable may be approximately 1.5 meters in length. Multiple coaxial conductor low noise cable(s) is generally not necessary, although it could be used, and an interconnecting multi-conductor cable that does not contain multiple coaxial conductors is preferred. This allows the interconnecting cable diameter to be reduced, providing greater cable flexibility and ease of use.

DESCRIPTION OF THE PREFERRED EMBODIMENT

Figure 1:
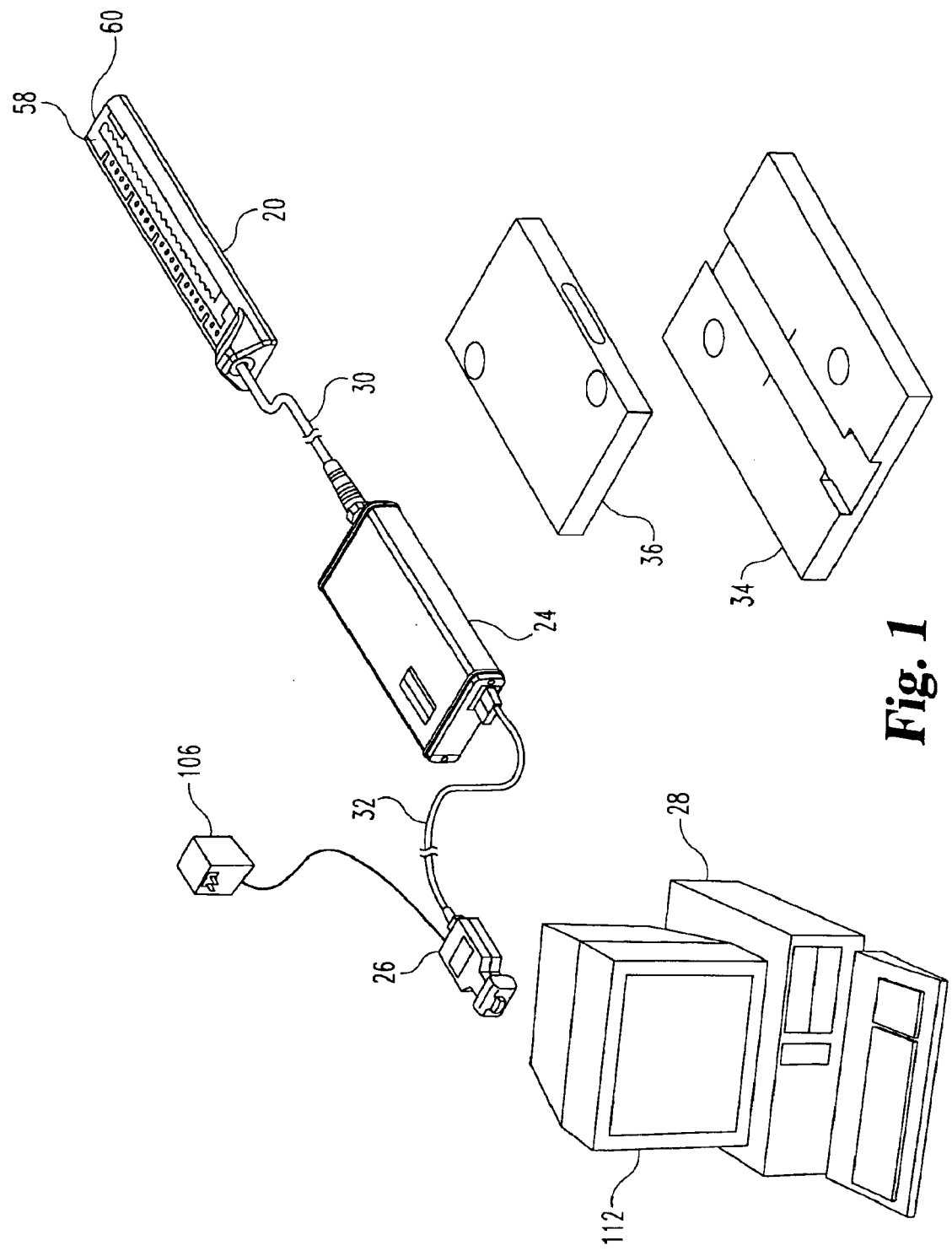
FIG. 1 shows a radiation detection system according to one embodiment of the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein, being contemplated as would normally occur to one skilled in the art to which the invention relates.

Referring generally to FIG. 1, an embodiment of a radiation detection system is shown, including an array 20 of radiation detectors 22, a signal processor 24, and an interface 26 that connects to a controller 28 (which may be a personal computer). Array 20 is connected to signal processor 24 via multi-conductor shielded cable 30, and in a specific embodiment the connection between array 20 and signal processor 24 is permanent. Signal processor 24 is connected to interface 26 through a multi-conductor cable 32. A gantry mounting plate 34 and buildup plate 36 may also be provided.

Figure 3A:
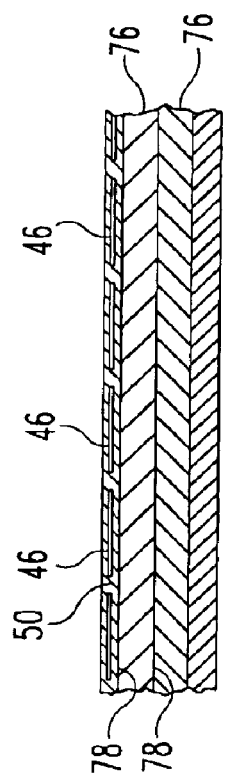
FIG. 3A is an enlarged cutaway view of an embodiment of a printed circuit board used in the embodiment of a linear array of detectors shown in FIG. 3.
Figure 3:
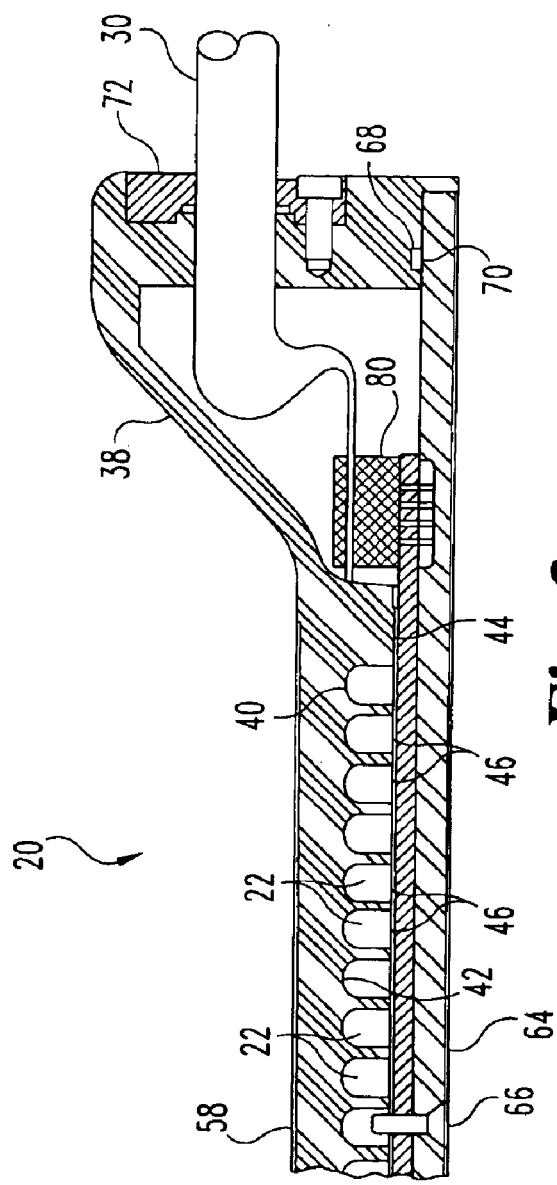
FIG. 3 is a left side cutaway view of an embodiment of a linear array of detectors used in the embodiment of the invention shown in FIG. 1.
Figure 4:
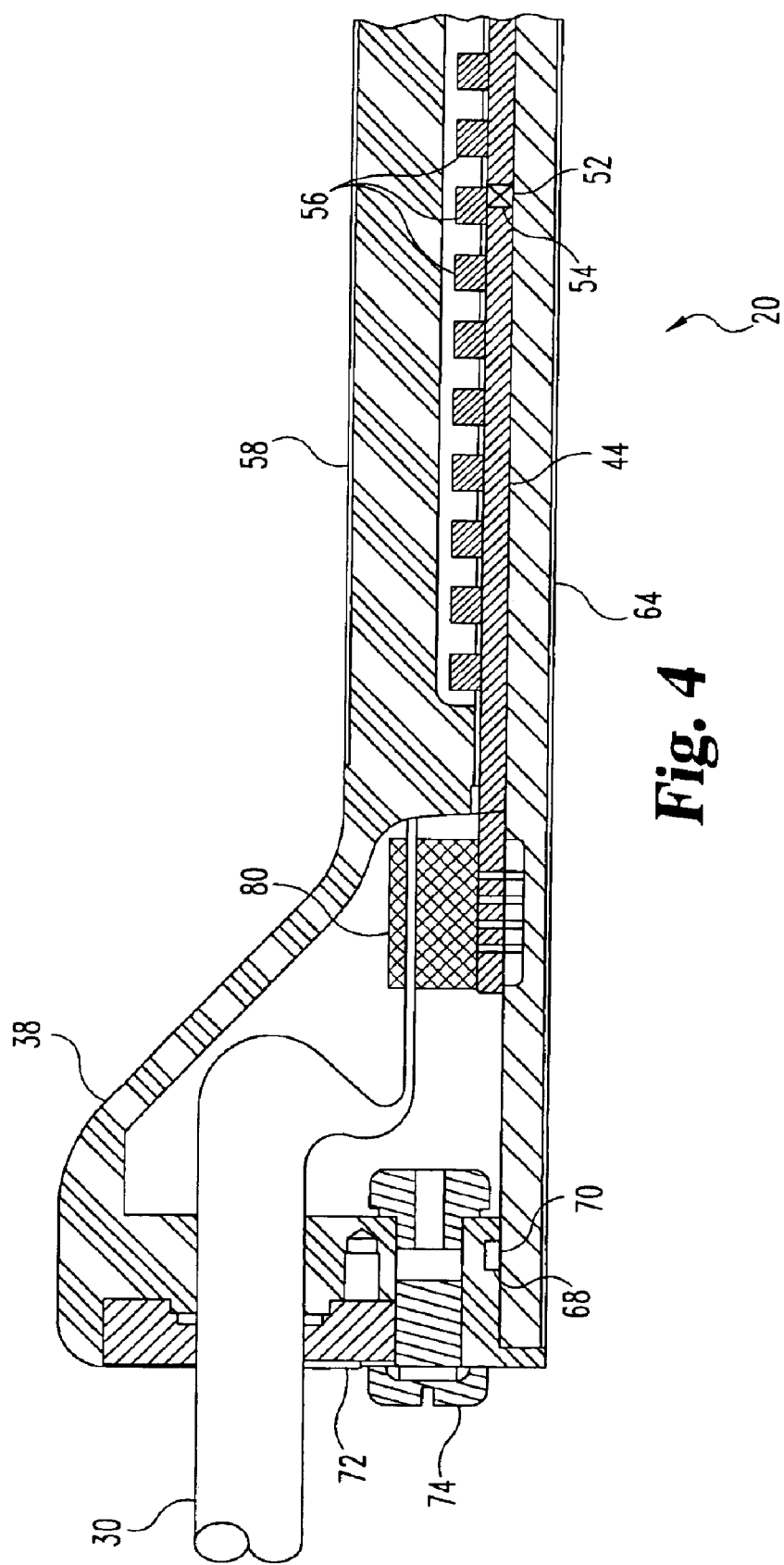
FIG. 4 is a right side cutaway view of the embodiment of a linear array of detectors shown in FIG. 2.

In the illustrated embodiment, array 20 is a waterproof, vented linear array of 47 detectors 22. Each detector 22 produces a signal (e.g. an electric current) that is proportional to the radiation exposure at its location. In a preferred embodiment, detectors 22 are ion chambers. Ion chamber detectors 22 may each have a radius of 0.5 cm, making the total active length of array 20 in this embodiment 23.5 cm. Ion chambers as a radiation detection device are known. A particular embodiment of such ion chambers may be seen in FIGS. 3 and 4. Ion chamber detectors 22 are formed in a molded housing 38. Each ion chamber detector 22 has a rounded rectangular cavity 40, and cavities 40 are linearly arranged parallel to an axis of housing 38. An electrically conductive coating 42 is applied to the inner surface of each cavity 40, and the conductive coating 42 of each cavity 40 is connected to the coating 42 of adjacent cavities 40. Electrically conductive coating 42 of each cavity 40 forms the cathode for each ion chamber detector 22 in array 20. An ionizing gas (for example air) is contained within the ion chamber volume, and a bias voltage applied to conductive surfaces 42 of cavities 40 to facilitate charge separation within the ionizing gas. Other embodiments of ion chambers are known, such as that disclosed in U.S. Pat. No. 5,508,526, which is incorporated herein by reference. Other detector apparatus is also known, such as those in U.S. Pat. Nos. 4,970,398 and 2,953,702, which are incorporated herein by reference, and principles are discussed in reference books such as "The Physics of Radiology" by Johns and Cunningham and "Introduction to Radiological Physics and Radiation Dosimetry" by Frank H. Attix.

Alternatively, some or all detectors 22 could be other known radiation detectors, for example solid state diodes, that provide an electric current proportional to the radiation density in proximity to the detector. Accordingly, in other embodiments array 20 could comprise a set of detectors 22 that are exclusively diodes, or that are a mixed set of diodes and ion chambers, or that include other types of detectors 22.

Array 20 further includes a circuit board 44, which in one embodiment is a multi-layer printed circuit board. Circuit board 44 includes an array (preferably a linear array) of electrically conductive collecting electrodes 46 located adjacent to each other and surrounded by an electrically conductive guard surface 48. Each electrode 46 is preferably planar and is separated from adjacent electrodes 46 and guard surface 48 by an insulator 50. Electrodes 46 and their insulators 50 are positioned on a surface (preferably the top surface) of circuit board 44 using known commercial printed circuit board manufacturing techniques. Each electrode 46 is connected to a detector 22 so that the signal produced by the detector when irradiated travels through the electrode. Electrical guarding between adjacent collecting electrodes 46 is accomplished by maintaining all of the collecting electrodes 46 at the same electrical potential as the surrounding guard. A key 52 molded into housing 38 fits into a detent 54 in circuit board 44 to accurately position circuit board 44 within housing 38.

An array of solid state detectors 56 are mounted, preferably linearly, on a surface of circuit board 44. When array 20 is irradiated, each solid-state detector 56 provides an output electrical signal. The signals from solid-state detectors 56 are connected together in parallel to provide a single electronic signal that is sent from array 20 along cable 30, as further described below. In this embodiment, solid-state detectors 56 are used only to indicate the existence of a radiation beam, not necessarily its intensity or other characteristics, and thus the performance degradation of solid-state detectors after long-term exposure to radiation is not a concern.

Housing 38 further preferably includes an indicator of the location of the center and outline of each cavity 40. In a particular embodiment, a decal 58 is affixed to housing 38 and includes such location indicators, such as hash marks or other markings. Numbers may also be provided to indicate the distance of a given mark from a fixed point such as the end of array 20, or a separate set of markings for indicating distance may be included. Housing 38 may include a slightly depressed area 60 to provide high accuracy in positioning decal 58. Instead of or in addition to decal 58, other types of location indicators may be provided, such as raised portions or indentations in a surface of housing 38.

The illustrated embodiment of housing 38 further includes a bottom cover 64 attached, for example, by nylon screws 66. As indicated above, housing 38 may be waterproof and/or vented. A groove 68 is located in bottom cover 64, and an O-ring 70 is placed in groove 68 to provide a waterproof seal when bottom cover 64 is attached to housing 38. Housing 38 may further include a waterproof cable strain relief 72 and vent port 74. A vent tube (not shown) may be connected to vent port 74 to provide vented operation of detectors 22 (e.g. ion chambers) in air or water, or vent port 74 may be sealed to provide sealed operation in air or water.

Circuit board 44, as indicated above, is preferably a multi-layer circuit board. Inner layers 76 include separate conductive paths (not shown) for conducting signals generated by electrodes 46 and solid-state detectors 56. Inner layers 76 (i.e. signal layers) are placed between two electrically-insulating guard layers 78. The conductive paths of circuit board 44 for the signals generated by the electrodes 46 and solid-state detectors 56 are connected to a mass terminated cable connector 80. In a specific embodiment, connector 80 is located at one end of circuit board 44. Electrically shielded multi-conductor cable 30 terminates in connector 80. Thus, in the embodiment in which array 20 includes 47 detectors, connector 80 will receive and pass 48 signals to cable 30, i.e., one signal for each detector 22, and one additional signal from solid-state detectors 56.

Figure 7:
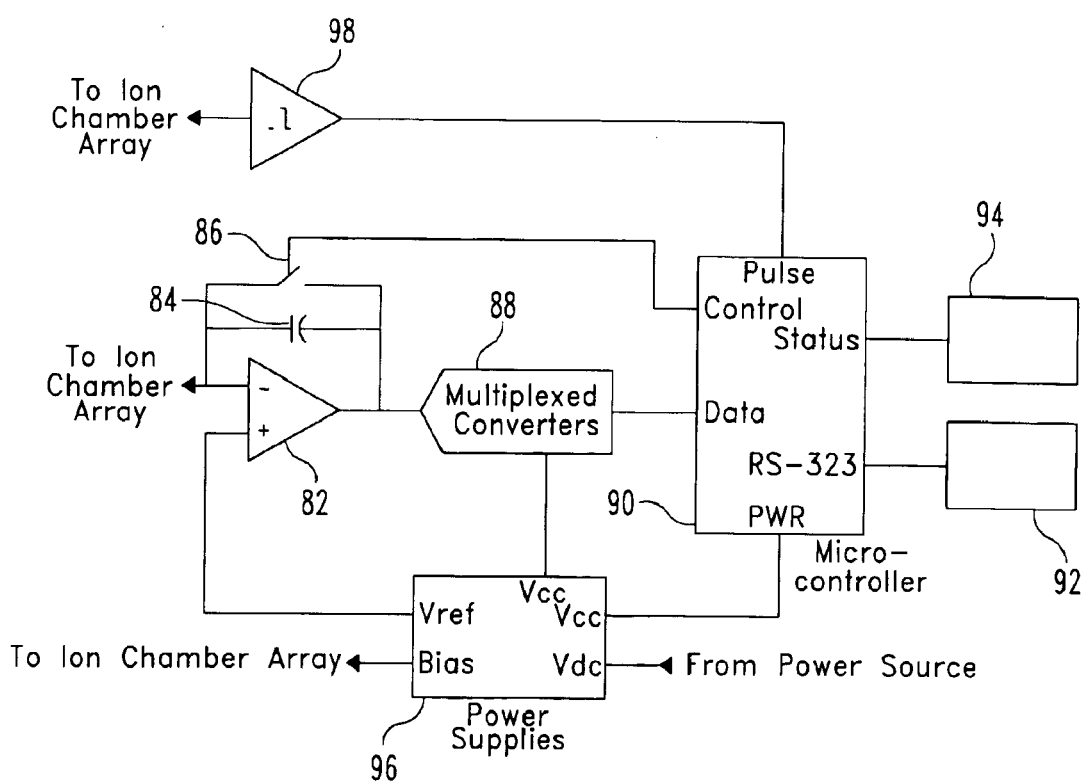
FIG. 7 is a block diagram showing the function of the embodiment of the signal processor shown in FIG. 5.

A preferred embodiment of signal processor 24 is a multi-channel processor shown schematically in FIG. 7. Signal processor 24 includes at least one electrometer 82 that receives the signals from one or more detectors 22. Preferably, signal processor includes one electrometer 82 for each detector 22. Each electrometer 82 has an associated integrating capacitor 84 and a solid-state switching circuit 86, and is connected to an analog-to-digital (A-to-D) converter 88. Switching circuit 86 is capable of resetting the integrated charge on capacitor 84 to zero by shorting it, i.e. discharging its accumulated charge. In the illustrated embodiment, A-to-D converter 88 is a multiplexed A-to-D converter, i.e. it includes a multiplexer, which allows conversion of analog signals from several electrometers 82 to their digital counterparts. In a specific embodiment, A-to-D converter 88 is an eight-channel multiplexed device, so that it can process signals from eight electrometers 82. In that embodiment, signal processor 24 would include six A-to-D converters 88 to be able to process signals from 47 electrometers 82 that are individually associated with 47 detectors 22.

The illustrated embodiment of signal processor 24 also includes a microcontroller 90, a communications interface 92, status LEDs (light emitting diodes) 94, power supply 96, and pulse detector 98. Microcontroller 90 has control outputs for switching circuit 86, communications interface 92 and status LEDs 94, and has inputs for pulses from pulse detector 98, power from supply 96 and data from A-to-D converter 88. Microcontroller 90 also includes memory of an amount and type sufficient to store calibration information concerning array 20 and/or signal processor 24, and to store digital data strings embodying information regarding radiation detected by detectors 22. Communications interface 92 is any appropriate interface allowing transfer of information from microcontroller 90 to cable 32, and may be an RS-485 interface in a particular embodiment. Status LEDs 94 operate under the control of microcontroller 90 to show whether and how signal processor 24 is functioning, e.g., that it is receiving, processing and/or outputting signals, information or other data. Power supply 96 provides high voltage bias supply for array 20 as well as power for A-to-D converters 88, electrometers 82 and microcontroller 90. Pulse detector 98 receives a signal from solid-state detectors 56 when radiation is being sensed, and sends a pulse to microcontroller 90. Pulse detector 98 is useful when testing a pulsed source of radiation, such as a linear accelerator.

In the illustrated embodiment, two communication interface connectors 99 are provided on signal processor 24, allowing multiple processors 24 to be connected simultaneously in a "daisy chain" connection. In such a connection, multiple processors 24 are connected in series, with an output of one signal processor 24 through one of its communication interface connectors 99 and a multi-conductor cable 32 inputted into an input communication interface connector 99 (see FIG. 6A). The end of signal processor 24 is then connected to controller 28 as described below. In a particular embodiment, communication interface connectors 99 are RJ-45 connectors.

Figure 8A:
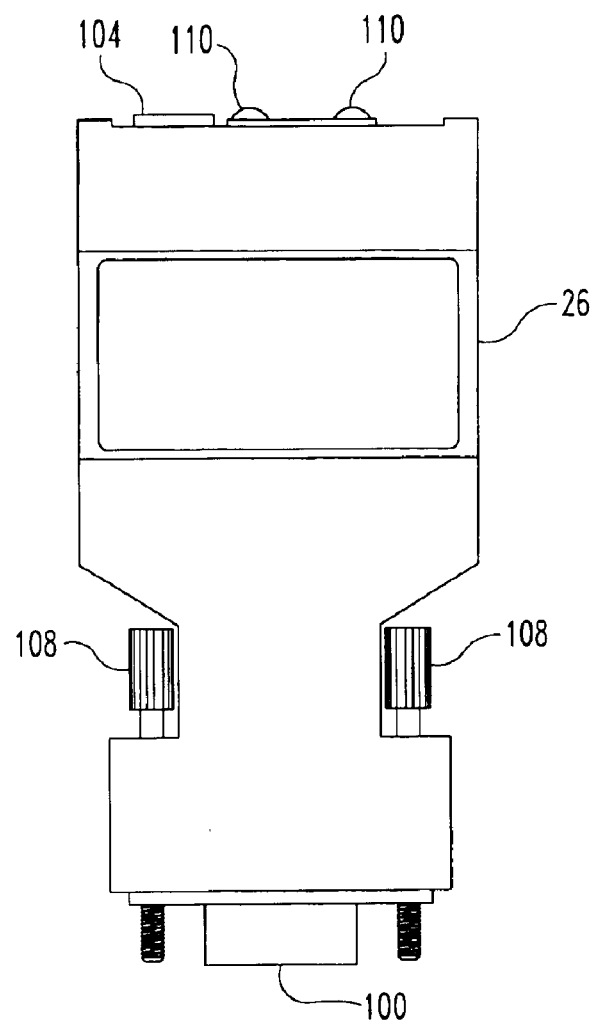
FIG. 8A shows a top view of an embodiment of a communicator device used in the embodiment of the invention shown in FIG. 1.
Figure 8B:
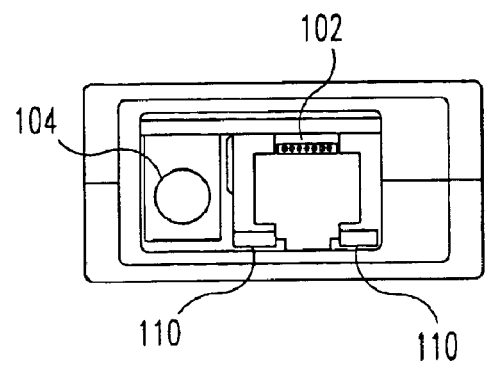
FIG. 8B shows an end view of the embodiment of a communicator device shown in FIG. 8A.
Figure 9A:
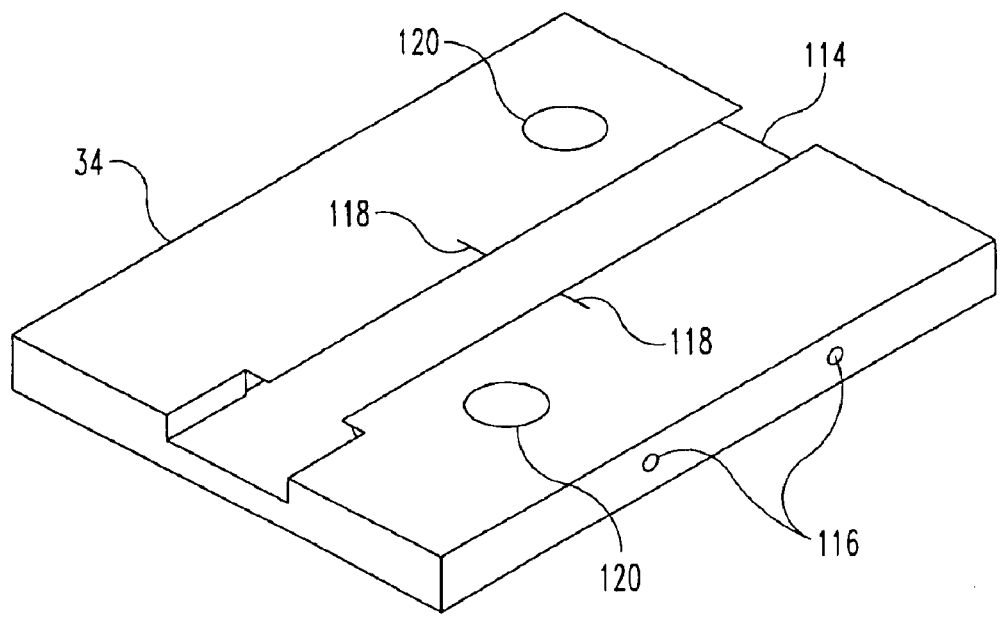
FIG. 9A shows an embodiment of a mounting plate used in the embodiment of the invention shown in FIG. 1.
Figure 9B:
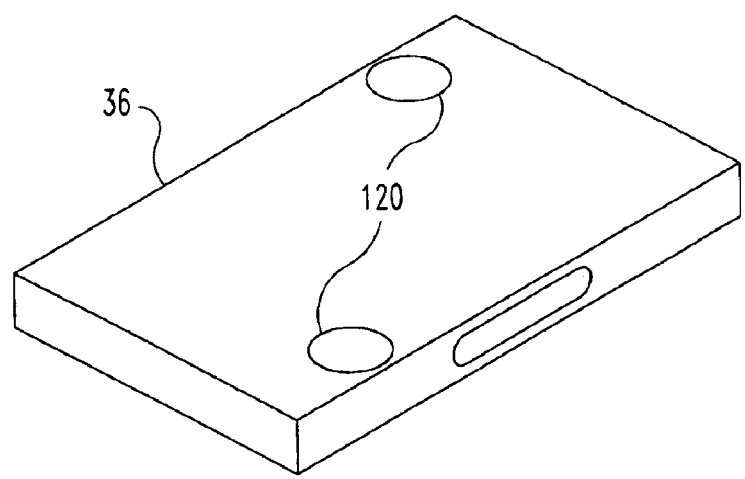
FIG. 9B shows an embodiment of a single buildup plate used in the embodiment of the invention shown in FIG. 1.

Referring now to FIGS. 1 and 8, interface 26 (also called a "communicator") translates and/or communicates signals between controller 28 and signal processor 24. For example, interface 26 may convert signals (e.g. RS-232 signals) of controller 28 into signals (e.g. RS-485 signals) usable by microcontroller 90 of signal processor 24, and may convert the digital signals sent by signal processor 24 into signals usable by controller 28. Interface 26 includes a communication interface connector 100 (e.g. a standard DB-9 RS-232 connector) for connecting to a communications port of controller 28 and a connection 102 for communication cable 32. In a particular embodiment, interface 26 provides power to supply 96 of signal processor 24 via cable 32 plugged into connection 102. Interface 26 may include a standard power supply connector 104, and may receive power from a power supply 106, such as a standard wall mount power supply. Thumbscrews 108 are provided to secure interface 26 to a communications port of controller 28 (e.g. a personal computer's RS-232 communications port). Status LEDs 110, which indicate communication status (data transmission and data received) are provided integral to connection 102.

Controller 28 is an electronic device capable of receiving data inputs from the signal processor 24 via interface 26 and utilizing such data to create a visual display or other output or format useful to a quality assurance technician. A preferred embodiment of controller 28 is a standard personal computer (PC) that includes at least one communications port (not shown), read-only and random access memory in which processing software is stored and can be operated for processing data received from signal processor 24, and a monitor 112 for displaying results. It will be seen that controller 28 may take other forms as well, such as a portable computer or smaller data analysis device, a larger computer, or other device dedicated to receiving data from signal processor 24 and generating a display of that data.

Figure 2:
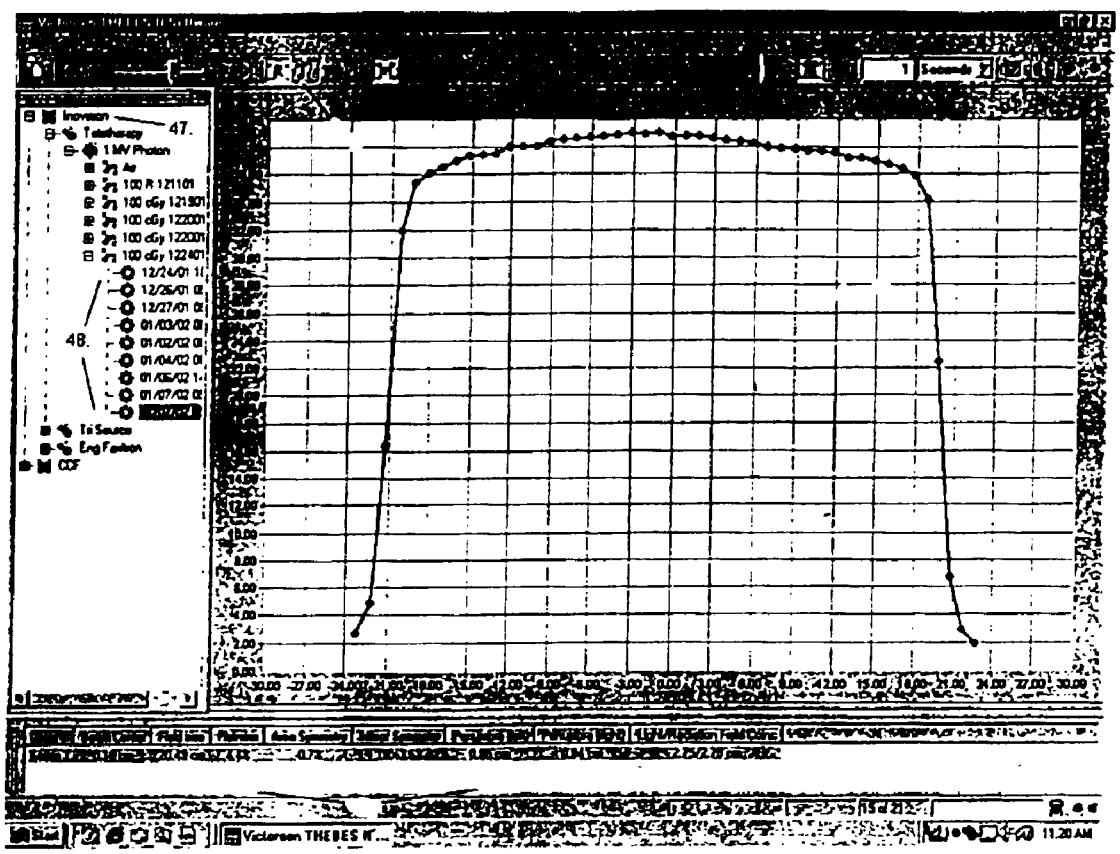
FIG. 2 shows a typical beam profile as analyzed and displayed by software.

In a preferred embodiment controller 28 has an associated monitor 112 or other display, and is loaded with software that receives beam profile and intensity data from array 20 via signal processor 24 and interface 26, and analyzes and displays the acquired data (FIG. 2) on monitor 112. The software may be a Windows-based application as shown in FIG. 2, but may be operable with other operating system(s) in addition to or instead of Windows. Beam profiles are acquired by controller 28 in frames, where each frame is a snapshot of the beam profile at a given moment in time. The frame rate is user settable and may be specified in seconds or appropriate electronic or radiation pulses, such as those of a linear accelerator. The software in controller 28 may display individual frames, and may display frames in succession via "playback" button(s) and/or slider control. The software preferably calculates and displays characteristics of a beam profile, such as values for beam center, field size, flatness, symmetry, area symmetry, mirror symmetry, penumbra (left and right), and light field/radiation field coincidence in real time. Such characteristics may be displayed in exposure rate units, integrated exposure units and normalized rate units. The software saves all frames acquired from an exposure in a database, and frames may be recalled to monitor 112 at any time. Multiple beam profiles may be recalled from the database and displayed simultaneously. Beam profiles may also be compared, with the result displayed as a percentage difference between the two profiles. Trend analysis may also be performed on a series of exposures.

As indicated in FIG. 1, in one embodiment array 20 is connected to signal processor 24 by a multi-conductor shielded cable 30. Cable 30 is of a sufficient length to allow signal processor 24 to be situated away from the radiation beam, and in a specific embodiment may be approximately 1.5 meters in length. Multiple coaxial conductor low noise cable(s) is generally not necessary, although it could be used, and an interconnecting multi-conductor cable that does not contain multiple coaxial conductors is preferred. Cable 30 in a preferred embodiment has a conductor for each detector 22, and an additional conductor for the output signal of solid-state detectors 56. Cable 30 carries the signals from detectors 22 in array 20 to corresponding electrometers 82 in signal processor 24. Cable 30 may also carry the detector bias voltage from supply 96 of signal processor 24 to detectors 22 in array 20. Cable 30 permanently connects signal processor 24 and array 20 in a particular embodiment (e.g. cable 30 is soldered to signal processor 24 and array 20), while in other embodiments cable 30 may be detachable from one or both of signal processor 24 and array 20. Controller 28 is connected to signal processor 24 by communication cable 32 and interface 26 that connects to a communications input in controller 28. Communication cable 32 may be a standard CAT-5 network cable with a length of up to 75 meters. In the embodiment in which controller 28 is a personal computer, interface 26 may connect to the computer's RS-232 communications port.

In embodiments in which it is desirable to mount array 20 to another device, for example a linear accelerator, a gantry mounting plate 34 may be provided. Mounting plate 34 has a slot 114 that array 20 fits into and has mounting holes 116 on its sides for attachment to gantry mounting brackets (not shown). Alignment marks 118 may be provided to assure proper alignment. Array 20 may thus be mounted directly to a linear accelerator (not shown), or indirectly via such mounting brackets. Mounting plate 34 is also used to position array 20 within a radiation beam. In a further embodiment, buildup plates 36 may be provided. Buildup plates 36 is preferably of acrylic and of a size of approximately 1 cm or 2 cm thickness. Buildup plates 36 are generally used to bring the ion chamber array into equilibrium by effectively thickening the ion chamber walls for use at higher energies, as is known in the art. They may be attached to mounting plate 34 and to each other so that they may be used in all positions. Mushroom-head fasteners 120 may be included with gantry plate 34 or buildup plate 36 to facilitate fastening.

Figure 5:
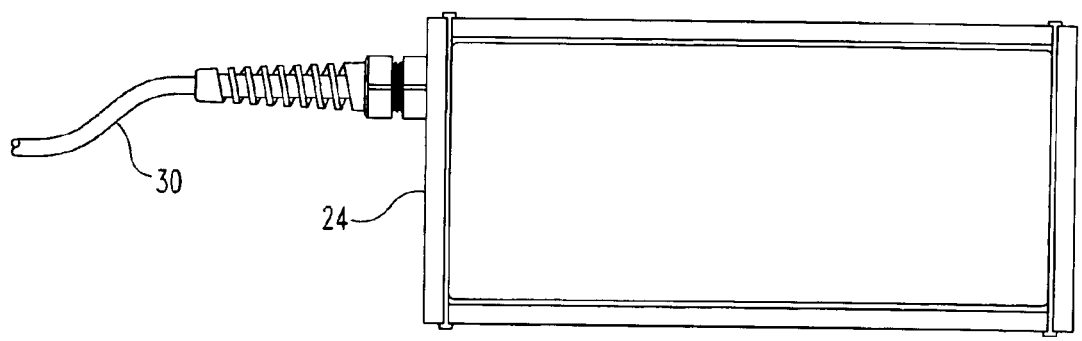
FIG. 5 is a front view of an embodiment of a signal processor used in the embodiment of the invention shown in FIG. 1.
Figure 6:
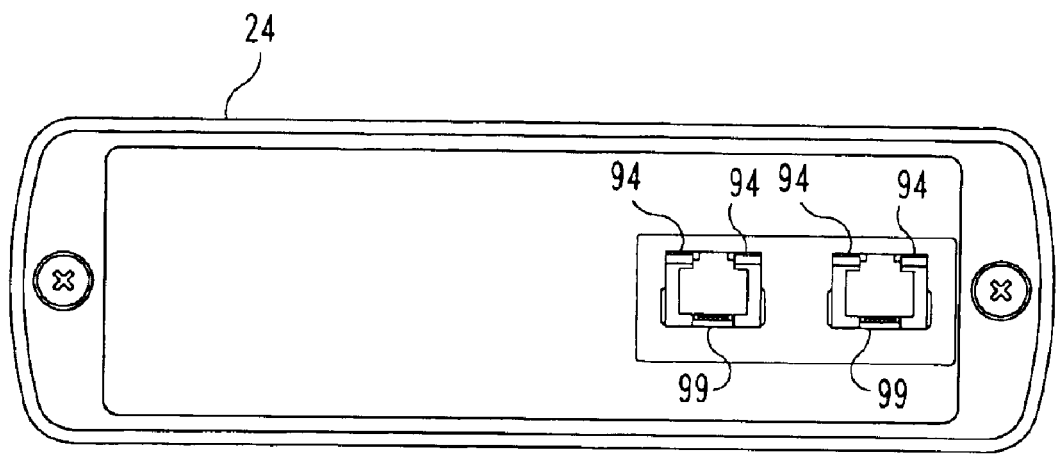
FIG. 6 is an end view of the embodiment of the signal processor shown in FIG. 5.
Figure 6A:
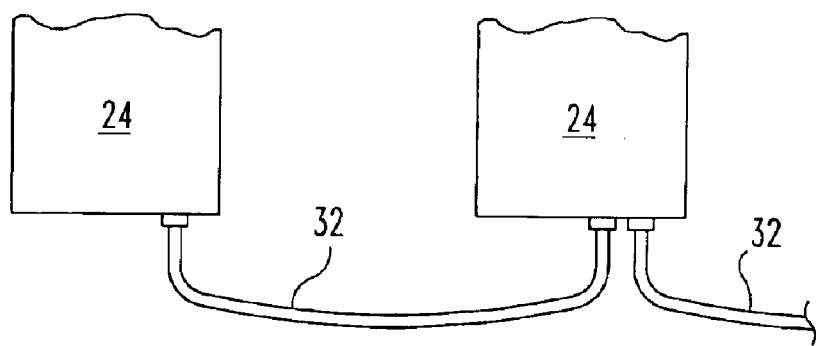
FIG. 6A is a top view of two signal processors of the embodiment shown in FIG. 5 connected together.

Referring now to FIGS. 1, 5 and 6, the operation of the disclosed system is described. Array 20 is placed in a position to intercept a radiation beam, for example a radiotherapy beam. Signal processor 24, interface 26 and controller 28 are positioned away from the radiation beam so as to prevent or reduce contact with radiation. Array 20, as indicated above, may be a linear array of radiation detectors 22, or alternatively may be an array of a different shape as may be required by a given beam, type of radiation, quality assurance test, or other parameter.

When radiation strikes array 20, an electric signal is generated by each detector 22 representing characteristic(s) of the radiation, and an electric signal is generated by solid-state detectors 56. In the embodiment in which detectors 22 are ion chambers, the radiation causes an electric charge to develop on coating 42, as is known in the art. As described above, the signal from each detector 22 is transferred via its respective electrode 46 to cable connector 80. The signals from the solid-state detectors 56 are connected in parallel to each other and transferred to cable connector 80. In the embodiment in which array 20 includes 47 detectors 22, cable connector 80 will have 48 connections, one associated with each detector 22 and one for the composite signal from solid-state detectors 56.

Cable connector 80 connects to shielded cable 30, which as described above may include a conductor for each signal that arrives at cable connector 80. The signals are passed via cable 30 to the signal processor 24, with each signal from a detector 22 being passed to its associated electrometer 82 and the signal from the solid-state detectors 56 being passed to pulse detector 98.

Referring now to FIGS. 1, 3, 4 and 7, signal processor 24 functions as follows. Each electrometer 82 integrates the signal (e.g. electric current) generated by its respective detector 22 (resulting from exposure of the respective detector 22 to radiation) on its integrating capacitor 84. The analog output voltage of each electrometer 82 is provided to an input of A-to-D converter 88, which converts the analog output voltage into its digital representation. Such digital representation will include data representing the strength of the radiation at the given detector 22, and may also include further data such as an indicator of the position of the detector 22 in array 20. Accordingly, in the embodiment in which array 20 has 47 detectors 22, there will be 47 analog voltage signals provided from electrometers 82 and 47 digital signals outputted from one or more A-to-D converters 88. The digital outputs from A-to-D converter(s) 88 are connected to the data input of microcontroller 90. The digital outputs may be stored in microcontroller 90 until called for by controller 28 or until a particular time has elapsed and microcontroller 90 sends the data. Alternatively, the digital outputs may be sent immediately to controller 28. Such output moves through communications interface 92 in microcontroller 90 and cable 32 to controller 28. Power supply 96 also supplies the reference voltage for electrometers 82 and the high voltage bias needed by detectors 22 (e.g. ion chambers) of array 20.

So long as array 20 is within a radiation beam, detectors 22 create electrical signals reflecting beam characteristics. Discrete measurements and processing of those signals occur in the signal processor 24. Microcontroller 90 initiates measurements and processing in the illustrated embodiment of signal processor 24. Microcontroller 90 can initiate measurements based on a passage of time, for example based on an internal timer or on a number of electrical pulses received from pulse detector 98. Pulse detector 98 receives the signal from the array of solid-state detectors 56 and generates a pulse output that indicates the presence of radiation on array 20. Thus, when the radiation beam to be tested is pulsed radiation, such as that from a medical linear accelerator, the signal from solid-state detectors will be intermittent. Pulse detector 98 can send a signal during or at the beginning or end of such signals, to inform controller 28 when the radiation beam is "on," and to allow controller 28 to determine the passage of time by counting pulses. In a particular embodiment, the measurement processes of the radiation detection system are timed with respect to such pulses to ensure that measurement and processing by signal processor 24 through electrometers 82 and A-to-D converters 88 of the signals sent from detectors 22 are made only between radiation pulses.

For ease of description, the measurement process will be described with respect to a single signal from a single detector 22. It will be understood that a similar or identical process will occur with signals from other detectors 22. When a measurement is initiated, microcontroller 90 opens switching circuit 86. Signals from detector 22 are integrated on integrating capacitor 84. The charge on integrating capacitor 84 determines the analog voltage output of electrometer 82. As noted above, integration may occur for a user-specified time period or for a number of radiation output pulses, and the timing is controlled by microcontroller 90. At the end of the integration period, the output of electrometer 82 is provided to A-to-D converter 88, under the control of microcontroller 90, converted to its digital representation, and stored in the internal memory of microcontroller 90. In the embodiment in which there are 47 electrometers 82, each corresponding to one detector 22, all 47 electrometers 82 can be read out in the time interval between radiation pulses at pulse repetition rates up to approximately 800 pulses per second. After the output of electrometer 82 has been measured, microcontroller 90 resets electrometer 82 by momentarily closing switching circuits 86, shorting integrating capacitor 84 and discharging its accumulated charge.

The data, representing a single scan of array 20, is formatted by microcontroller 90 into a data string and transferred to controller 28, via communication cable 32 and interface 26. For example, microcontroller 90 may send data strings via its communications interface 92 (e.g. an RS-485 interface) to interface 26, which converts the RS-485 digital signal to RS-232 for use in controller 28. A cyclic redundancy checksum (CRC) is utilized to ensure data integrity. The data stream is received by controller 28, parsed, and each measurement of a detector 22 is offset-adjusted and converted to radiation exposure units by applying calibration factors. The calibration factors are permanently stored in non-volatile memory of microcontroller 90 and imported by controller 28 when the analysis and display software is started. The beam profile and intensity data is then displayed and analyzed by the software (FIG. 2).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. For example, cable 30 is described in one embodiment as a multi-conductor shielded cable. Cables with fewer than one conductor per radiation detection apparatus could be used, with electronic switching or other features provided to insure that the signals from each detector do not interfere with each other. Controller 28 is described as a PC, but it will be understood that any type of computer or data analysis and display device could be used. Display of data received by controller 28 can occur on a printer, projection system, or other display apparatus as well as a PC monitor.

What is claimed is:

1. An apparatus for detecting a radiation beam comprising:

a plurality of first radiation detectors forming an array adapted to generate an instantaneous electrical current proportional to the instantaneous radiation rate at the associated one of said radiation detectors;

a signal processor connected to said array and located at a distance from said array sufficient to avoid substantial contact with the radiation beam, said signal processor having multiple channels for making measurements of said currents generated by each of said first radiation detectors and to communicate said measurements, each of said channels including an electrometer;

a set of second radiation detectors, said set including multiple solid-state radiation detectors connected together in parallel to provide a single electronic signal, said signal being transmitted to said signal processor;

a housing having a longitudinal axis, wherein said array of first radiation detectors are ion chambers arranged substantially linearly in said housing to one side of said axis, and said set of second radiation detectors being arranged substantially linearly in said housing to the other side of said axis;

a controller communicatively connected to said signal processor and adapted to receive said measurements;

a first multi-conductor cable connecting said array to said signal processor; and a second multi-conductor cable and communication interface device, which connects one or more of said electrometers to said controller.

2. The apparatus of claim 1, wherein said ion chambers are formed in said housing, and each said ion chamber includes a cavity having an inner surface with an electrically conductive coating applied thereto, wherein the electrically conductive coating of each cavity are connected together to form the cathode of each ion chamber.

3. The apparatus of claim 1, further comprising a circuit board having an array of electrically conductive collecting electrodes and an electrically conductive guard surface, said electrodes being separated from each other and from said guard surface by at least one insulator.

4. The apparatus of claim 3, wherein said housing has an exterior including an indicator of at least one of the location and the outline of said cavities.

5. The apparatus of claim 4, wherein said housing further includes a vent port capable of connection to a vent tube and alternatively of sealed operation.

6. The apparatus of claim 5, wherein said circuit board includes at least one inner layer that includes said electrodes between two insulating layers.

7. The apparatus of claim 1, comprising two signal processors connected in series, with an output of a first signal processor inputted into a second signal processor, and the output of said second signal processor connected to said controller.

8. The apparatus of claim 1, wherein said array of radiation detectors is connected to said signal processor by a multi-conductor shielded cable, said cable having at least one conductor associated with each individual detectors.

9. The apparatus of claim 8, wherein said cable includes an additional conductor for said signal of said solid-state detectors.

10. The apparatus of claim 1, further comprising a circuit board connected to said array, said circuit board having at least one circuit for conducting said currents from at least one of said first radiation detectors.

11. The apparatus of claim 10, wherein said circuit board includes at least one circuit for conducting said signal from said set of second radiation detectors.

12. The apparatus of claim 1, wherein said signal processor includes at least one analog-to-digital converter connected to said electrometers.

13. The apparatus of claim 12, wherein said analog-to-digital converter is a multiplexed analog-to-digital converter.

14. The apparatus of claim 1, further comprising a display medium communicatively connected to said signal processor, whereby information relating to said measurements can be displayed.

15. The apparatus of claim 1, further comprising a mounting plate having a slot into which said housing fits, and mounting holes adapted for at least one of direct and indirect attachment to a radiation source.

16. The apparatus of claim 15, further comprising at least one buildup plate connected to said mounting plate.

17. An apparatus for detecting a radiation beam comprising:
- a plurality of first radiation detectors forming an array adapted to generate an instantaneous electrical current proportional to the instantaneous radiation rate at the associated one of said radiation detectors;
- a signal processor connected to said array and located at a distance from said array sufficient to avoid substantial contact with the radiation beam, said signal processor having multiple channels for making measurements of said currents generated by each of said first radiation detectors and to communicate said measurements, each of said channels including an electrometer;
- a set of second radiation detectors adapted to generate a signal, said set including at least one such detector, and said signal being transmitted to said signal processor;
- a controller communicatively connected to said signal processor and adapted to receive said measurements; and
- a housing having a longitudinal axis, wherein said array of first radiation detectors are ion chambers arranged substantially linearly in said housing to one side of said axis, and said set of second radiation detectors being arranged substantially linearly in said housing to the other side of said axis.

18. The apparatus of claim 17, wherein said ion chambers are formed in said housing, and each said ion chamber includes a cavity having an inner surface with an electrically conductive coating applied thereto, wherein the electrically conductive coating of each cavity are connected together to form the cathode of each ion chamber.

19. The apparatus of claim 17, further comprising a circuit board having an array of electrically conductive collecting electrodes and an electrically conductive guard surface, said electrodes being separated from each other and from said guard surface by at least one insulator.

20. The apparatus of claim 19, wherein said housing has an exterior including an indicator of at least one of the location and the outline of said cavities.

21. The apparatus of claim 20, wherein said housing further includes a vent port capable of connection to a vent tube and alternatively of sealed operation.

22. The apparatus of claim 19, wherein said circuit board includes at least one inner layer that includes said electrodes between two insulating layers.

23. The apparatus of claim 17, comprising two signal processors connected in series, with an output of a first signal processor inputted into a second signal processor, and the output of said second signal processor connected to said controller.

24. The apparatus of claim 17, wherein said array of radiation detectors is connected to said signal processor by a multi-conductor shielded cable, said cable having at least one conductor associated with each individual detectors.

25. The apparatus of claim 24, wherein said cable includes an additional conductor for said signal of said solid-state detectors.

26. The apparatus of claim 17, further comprising a circuit board connected to said array, said circuit board having at least one circuit for conducting said currents from at least one of said first radiation detectors.

27. The apparatus of claim 26, wherein said circuit board includes at least one circuit for conducting said signal from said set of second radiation detectors.

28. The apparatus of claim 17, wherein said signal processor includes at least one analog-to-digital converter connected to said electrometers.

29. The apparatus of claim 28, wherein said analog-to-digital converter is a multiplexed analog-to-digital converter.

30. The apparatus of claim 17, further comprising a display medium communicatively connected to said signal processor, whereby information relating to said measurements can be displayed.

31. The apparatus of claim 17, further comprising a mounting plate having a slot into which said housing fits, and mounting holes adapted for at least one of direct and indirect attachment to a radiation source.

32. The apparatus of claim 31, further comprising at least one buildup plate connected to said mounting plate.

33. The apparatus of claim 17, further comprising a multi-connector cable connecting said array to said signal processor.

34. The apparatus of claim 17, further comprising a multi-conductor cable which connects one ore more of said electrometers to said controller.

35. The apparatus of claim 17, further comprising a communication interface device communicatively connected one or more of said electrometers and said controller.

* * * * *

UNITED STATES PATENT AND TRADEMARK OFFICE
CERTIFICATE OF CORRECTION

PATENT NO. : 6,885,007 B2
DATED : April 26, 2005
INVENTOR(S) : Donaghue et al.

It is certified that error appears in the above-identified patent and that said Letters Patent is hereby corrected as shown below:

Column 14,
Line 2, delete "ore" and insert -- or -- between "one" and "more".

Signed and Sealed this

Thirty-first Day of January, 2006

JON W. DUDAS
*Director of the United States Patent and Trademark Office*